US007949476B2

(12) United States Patent
Strubel et al.

(10) Patent No.: US 7,949,476 B2
(45) Date of Patent: May 24, 2011

(54) METHOD FOR ESTIMATING MOLECULE CONCENTRATIONS IN A SAMPLING AND EQUIPMENT THEREFOR

(75) Inventors: Gregory Strubel, Manosque (FR); Jean-Francois Giovannelli, Bordeaux (FR); Pierre Grangeat, Saint Ismier (FR)

(73) Assignee: Commissariat a l'Energie Atomique, Paris (FR)

( * ) Notice: Subject to any disclaimer, the term of this patent is extended or adjusted under 35 U.S.C. 154(b) by 112 days.

(21) Appl. No.: 12/195,848

(22) Filed: Aug. 21, 2008

(65) Prior Publication Data

US 2009/0055101 A1     Feb. 26, 2009

(30) Foreign Application Priority Data

Aug. 22, 2007   (FR) ...................... 07 57131

(51) Int. Cl.
*G01N 33/68* (2006.01)
(52) U.S. Cl. .............. 702/23; 702/19; 702/181
(58) Field of Classification Search .................. 702/19, 702/21, 22, 23, 25, 27, 28, 30–32, 179, 181; 435/4; 422/50–99; 204/400–435; 205/775–794.5; 703/11, 12; 436/86, 161, 173; 73/1.01–1.07
See application file for complete search history.

(56) References Cited

U.S. PATENT DOCUMENTS

| 5,616,504 A * | 4/1997 | Brown et al. ................ 436/518 |
| 2005/0256650 A1* | 11/2005 | Labarbe et al. ................ 702/19 |
| 2008/0015793 A1* | 1/2008 | Ben-Menahem et al. ...... 702/30 |

FOREIGN PATENT DOCUMENTS
EP        1 598 666 A1    11/2005

OTHER PUBLICATIONS

H. D. Kang, et al., "Decomposition of Multicomponent Mass Spectra Using Bayesian Probability Theory", Journal of Mass Spectrometry, XP002476266, Jul. 2002, vol. 37, pp. 748-754.
T. Schwarz-Selinger et al., "Analysis of Multicomponent Mass Spectra Applying Bayesian Probability Theory", Journal of Mass Spectrometry, XP002476267, Aug. 2001, vol. 36, pp. 866-874.
Said Moussaoui et al., "Separation of Non-Negative Mixture of Non-Negative Sources Using a Bayesian Approach and MCMC Sampling", IEEE Transactions on Signal Processing, XP002476268, vol. 54, No. 11, Nov. 2006, pp. 4133-4145.
A. Mohammed-Djafari, et al., "Regularization, Maximum Entropy and probabilistic Methods in Mass Spectrometry Data Processing Problems", International Journal of Mass Spectrometry, XP004346683, vol. 215, No. 1-3, pp. 175-193.
Melanie Hilario, et al., "Processing and Classification of Protein Mass Spectra", Mass Spectrometry Reviews, XP002476269, Feb. 2006, vol. 25, pp. 409-449.

* cited by examiner

*Primary Examiner* — Mohamed Charioui
*Assistant Examiner* — Ricky Ngon
(74) *Attorney, Agent, or Firm* — Oblon, Spivak, McClelland, Maier & Neustadt, L.L.P.

(57) ABSTRACT

A method for estimating molecule concentrations in a sample, the method including: obtaining a signal generated by a sample analyzing apparatus, the signal including at least one spectrum, the spectrum including peaks representative of the molecule concentrations in the sample and being expressed as a function of at least one variable; obtaining an analytical modeling of the signal with a modeling function, wherein the modeling function is based on the molecule concentrations and factors including gain factors of the equipment and description factors of the peaks; selecting uncertain factors in the factors; determining a priori probability distributions for the uncertain factors and the molecule concentrations; establishing, with the modeling function and the signal, posteriori probability distributions for the molecule concentrations and the uncertain factors; and estimating, with a processing module, the molecule concentrations and the uncertain factors from a parameter inferred from the posteriori probability distributions.

16 Claims, 2 Drawing Sheets

METHOD FOR ESTIMATING MOLECULE CONCENTRATIONS IN A SAMPLING AND EQUIPMENT THEREFOR

BACKGROUND

1. Technological Field

This invention relates to a method for estimating molecule concentrations in a sampling, and the equipment therefor.

2. Description of Related Art

Some apparatuses enable to separate the detection of different molecules in a sample along a signal that is a spectrum. The detected components typically appear as peaks whose height depends on the concentration of the molecule concerned in the sample. The liquid phase chromatographs and the mass spectrometers have this property by separating the molecules from their retention time in the column and their mass divided by the charge respectively. The apparatuses can be used together, and the resulting signal is then a multiple spectrum, showing a peak scattering on a plane as a function of the two parameters.

The measurements can be difficult to exploit because of the high number of molecules present in the sample and of the existence of isotopes that change the mass of some measured molecules with respect to their usual value and modify the peak shapes to give isotopic ranges that are less recognizable and less easy to measure. Another difficulty arises for elements that are present in a very low concentration and yet whose detection is sometimes necessary. The conventional signal analyses can then fail.

A conventional method consists thus in inferring a concentration of a molecule from the height or the area of its peak on the signal.

Another method consists of analysing the whole signal by a spectral analysis by making comparisons with a library of known spectra.

It is understood that these methods can result in insufficient results for peaks that are weakly marked by low concentration molecules, because of the noise of the signal or of the superimposing with surrounding peaks.

Other methods are based on probabilistic estimations including in particular Bayesian analyses. The mathematical problem $y=Hx+b$, where y refers to the measurements, H an inversion matrix, x the result to be found (magnitudes to be assessed) and b the noise, is solved in Kang, Preuss, Schwarz-Selinger and Dose paper, entitled "Decomposition of multi-component mass spectra using Bayesian probability theory" (published in Journal of mass spectrometry, volume 37, July 2002, pages 748, 754), by assessing the noise as a Gaussian function of zero average and determined variance which results in an expression of the magnitudes of vector x in the form of a probability distribution. Moussaoui, Brie, Moahammed-DJafari, Carteret paper "Separation of Non-Negative Mixture of Non-Negative Sources Using a Bayesian Approach and MCMC Sampling" (published in IEEE transactions on signal processing, volume 54, November 2006, pages 4133 to 4145), and Mohammad-Djafari and al. paper "Regularization, maximum entropy and probabilistic methods in mass spectrometry data processing problems" (published in International Journal of mass spectrometry, volume 215, number 1 to 3, 1 Apr. 2002, pages 175 to 193), describe generalizations in which the coefficients of the matrix H are also considered as uncertain and modelled by different probability distributions. Such methods lead to numerous calculations since the number of coefficients is typically equal to the number of measurement points on the signal multiplied by the number of magnitudes to be assessed. Allocating a priori probability distributions to each of the coefficients of the matrix is arbitrary and can lead to results that are not very representative. Further constraints should generally be introduced to be able to solve the problem, however the data necessary to properly and accurately introduce them are often missing. As a result, these prior art methods do not ensure a suitable result despite of their will to express their results as the more realistic form of the probability distributions.

SUMMARY

The invention is based on a different idea: modelling the measured signal as a function of parameters with, among other things, gain factors of the equipment, description factors of the peaks that make up the signal (their position on the signal or their shape) and possibly other factors, such as the molecule distributions as a function of variation in atomic mass or electrical charge for each of them, noise, etc. The mathematical problem is then solved with much less unknowns since these factors are in a rather small number, and most often correspond to a small number of modelling points. The parameters can often be estimating in calibration steps preceding the so called measurement and be assessed with high accuracy that enables to allocate them a priori reliable probability distributions.

The invention can be implemented with numerous variants according to constraint factors as uncertain among the model factors and then to which are allocated probability distributions. If these factors are in a relatively small number, solving the model can be simple, otherwise more complicated calculations will be necessary. A direct resolution could be contemplated with a small number of uncertain factors, otherwise an alternative resolution will be often necessary, with the probability distributions depending upon each other: the calculation will consist in converging the parameters of these probability distributions towards limit values and the final results of the concentrations will be obtained anyway by an estimation taking into account these parameters.

It is an advantage of the invention that the whole signal is used in searching the results and not only portions including the peaks of measurements. It is another advantage that the model is comprehensive and reliable, with the intervention of all the factors responsible for providing the signal.

The probability distributions can be explicit if they are expressed by conventional statistical laws, or empirically obtained by applying random numbers is they depend on complex functions.

Under the most general form, the invention relates to a method for estimating molecule concentrations in a sample, consisting of allowing the sample to go through an equipment and thus obtaining a signal consisting of at least one spectrum composed of peaks, representative of molecule concentrations as a function of at least one variable and in estimating the molecule concentrations; characterised in that it consists of carrying out an analytical modelling of the signal with a modelling function comprising factors, whose concentrations and other factors include gain factors of the equipment, description factors of the peaks; and then allocating to the concentrations and to some other factors, which are uncertain factors, a priori probability distributions; inferring from the signal a posteriori probability distributions for the concentrations, by using the modelling function, the estimations of the other factors and the a priori probability distributions, and estimating the concentrations from a parameter inferred from the a posteriori probability distributions.

The decision parameter inferred from the a posteriori distributions can be an average, a median, or the argument corresponding to the maximum value of the distribution for example; the a priori probability distributions can include Gaussian functions or other known statistics; the a posteriori probability distributions can be such functions, or be empirically obtained by generating random numbers.

Another aspect of the invention is the distribution of factors of the signal analytical model into factors deemed as stable (constant with the same equipment regardless of the experiment) and unstable (variable from one experiment to another). All these factors can be or can not be considered as uncertain in the sense of the invention and then be applied to probability distributions. The stable factors can be subjected to an external calibration consisting of an injection of molecules similar to some molecules of the sample, but with known concentrations, into the equipment (in the absence of the sample) and inferring some other factors from a signal of the calibration injection and the analytical model. It should be emphasized that the external calibration can also be carried out by probabilistic calculations implying probability distributions for the factors of the analytical model, this time applied to the calibration injection, except for the molecule concentrations that are well determined this time.

The invention can also include an internal calibration consisting of an injection of marker molecules into the sample, the marker molecules having respectively properties similar to some molecules of the sample with respect to the equipment and giving measurement peaks close to measurement peaks of said some molecules of the sample.

The distribution into stable and unstable factors can be decided by the user from the nature of the equipment, the conditions of the experiments and its own knowledge. That is why the signal's level gain by the equipment is normally unstable, as well as the retention times of the molecules by the chromatographic column when used.

Another aspect of the invention is an equipment in which the method is carried out to obtain the molecular profile of the sample.

The invention will now be explained according to an application for which it has been first designed: the measurement of proteins in biological fluids, for which the previous problems sharply appeared because of the great number of proteins that can been encountered and the very low concentration of some of them, whereas an accurate measurement is desired nevertheless because some of them can be decisive to establish a medical diagnosis or the like. Proteins are thus cancer markers.

DETAILED DESCRIPTION

Figure 1:
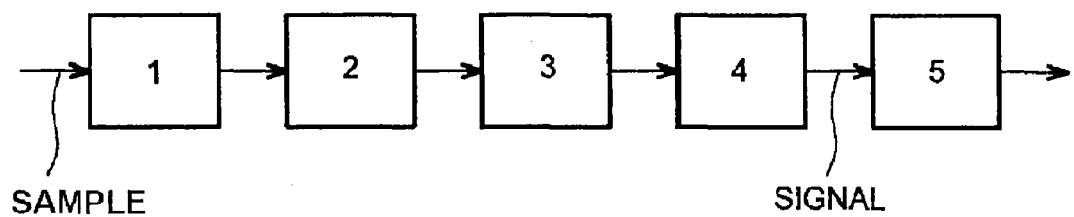
FIG. 1 is a diagram of the measurement equipment,
FIG. 2 an illustration of a signal and
FIG. 3 a flowchart.
Figure 2:
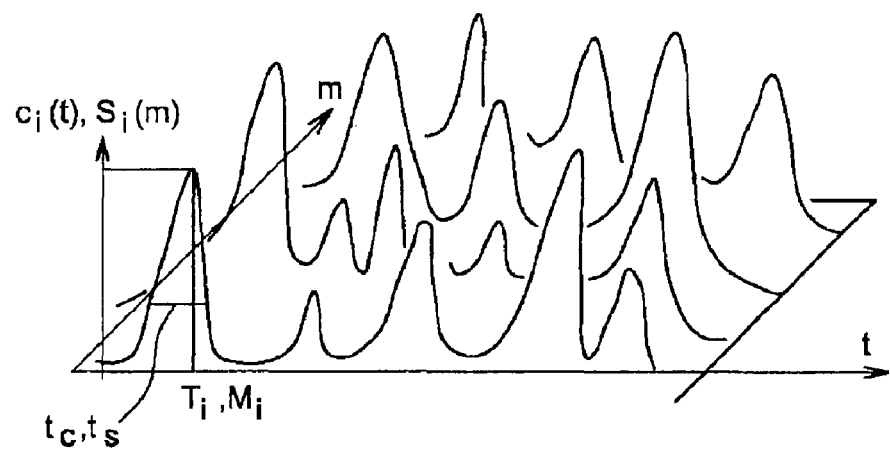

The whole measurement line is schematically represented in FIG. 1. A blood or plasma sample is provided to a preparation module 1, that is used to separate the molecules that will be subjected to the measurement of the remainder of the sample. Processes of biological or physical nature, such as picking up some proteins by affinity with antibodies, can be employed. The selected protein mixture goes then through the measurement equipment, that first includes a digestion module 2 breaking down the proteins into peptides or amino acids and reducing their mass, a liquid phase chromatograph 3 that separates the proteins from each other, gives a first measurement and possibly enables another selection of proteins, and a mass spectrometer 4 which provides a second measurement. The digestion module 2 is functional, and only one of the measurement means 3 and 4 can be employed. The measurements consist of a spectrogram of proteins (FIG. 2) that an information processing module 5 receives, whose operation will be now described and that provides results interpreted by the user.

A first element of the invention is the construction of an analytical model of the measurement line. In the case of FIG. 1, where the protein mixture is analysed according to two dimensions corresponding to two physico-chemical parameters, with the model integrating parameters associated with chromatograph 3 and mass spectrometer 4.

A chromatographic column is a system that differently slows down each of the molecules that travels through it. The input and the output of this system are functions representing a molecular quantity as a function of time. The propagation of proteins in the column can be described by a differential equation that can thus be approximated by the convolutive model with a Gaussian impulse response whose average $T_i$ is called retention time of the protein i. The output signal of the protein $C_i(t)$ can thus be described by the equation (1)

$$c_i(t) = (2\pi \gamma_c^{-1})^{-1/2} \exp(-0.5\gamma_c(t-T_i)^2)$$

where $\gamma_c$ is the reciprocal of the variance of the Gaussian response. The retention times $T_i$ are considered as unstable from one measurement to another; therefore, it is difficult to directly identify the natures of the proteins associated with each of the peaks, but marker molecules can be used, whose concentration is known and composition is close to the proteins being searched for, that are injected with the sample into the chromatographic column to detect their peaks, which are adjacent to those of said close proteins, that are thus identified.

The output of the chromatographic column is constantly analysed by the mass spectrometer 4. It is sensitive to the ratio between the mass of a molecule and its charge, and outputs a function giving the molecule quantity in the sample according to their mass to charge ratio.

Each protein will be generally formed from several impulses because of isotopes that can give different masses to a same molecule. Moreover, the ionisation phenomenon can give them a different number of charges. Conventionally, a protein can have up to three neutrons and three further charges.

The output signal of the mass spectrometer 4 can be modelled by the equation (2)

$$s_i(m) = \sum_{j=1}^{3} \sum_{k=0}^{3} \Pi_{ijk} \exp\left(-0,5\gamma_s\left(m - \frac{M_i + kM_n}{j}\right)^2\right)$$

with $$\Pi_{ijk} = \frac{\gamma_s^{1/2} \pi_{ij} \pi'_{ik}}{(2\pi)^{1/2}}, \sum_j \pi_{ij} = 1 \text{ and } \sum_k \pi'_{ik} = 1,$$

where the parameters are:
j, number of charges carried by the protein,
k, number of further neutrons,
$\Pi_{ij}$, proportions of the protein i having j charges,
$\Pi_{ik}$, proportions of the protein i having k further neutrons,
$\gamma_s$, reciprocal of the variance of the spectrometric peaks,
$M_i$, mass of the protein i without further neutrons,
$M_n$, mass of a neutron.

The overall signal model reaching the information processing module 5 can thus be represented by the equation (3) when the digestion module 2 is present:

$$Y = \sum_{p,i,j} (x_p D_{ip} \Xi_i \pi_{ij} s_{ij} c_i^t + x_p^* D_{ip} \Xi_i \pi_{ij} s_{ij}^* c_i^t) + B,$$

where the symbols representing the measured signal are:
p: number of the protein being studied,
i: number of the peptide being studied,
j: number of charge carried by the peptide being studied,
Y: data: spectrogram,
B: noise,
$X_p$: concentration of the protein p in the analysed sample,
$X_p^*$: concentration of the weighed down version of the protein p, that is isotopic to the protein p, of the real sample, but added as an internal calibration into the analysed sample,
$D_{ip}$: gain of the digestion and of the preparation steps of the protein into peptides (ideally a natural integer),
$\Xi_i$: gain of the system for the peptide i,
$\pi_{ij}$: proportion of the peptide i having the charge j,
$S_{ij}^*$: mass spectrum of the peptide i charged j times, sampled form of the signal $S_{ij}$ (m) where $$s_{ij}(m) = \sum_{k=0}^{3} \Pi_{ik} \exp\left(-0,5\gamma_1 \left(m - \frac{M_i + kM_n}{j}\right)^2\right) \text{ and } \Pi_{ik} = \frac{\gamma^{1/2} \Pi'_{ik}}{(2\pi)^{1/2}},$$

to be compared to the equation (2),
$S_{ij}$: mass spectrum of the peptide weighed down i charged j times,
$c_i^t$: transpose of the chromatogram of the peptide i, sampled form of the signal $c_i(t)$, expressed as a vector.

The model is linear depending on the protein or peptide concentrations, and the part related to the mass spectrometer 4 is independent on the one related to the chromatograph 3. Using only one of the apparatuses would thus be immediately exploitable by simplifying the model. Moreover, the influence of the digestion module 2 appears through the coefficient $D_{ip}$ that would disappear from the formula for a system without this model; only proteins would be considered instead of peptides, without changing the invention.

The model of the equation (3) can be represented in a simplified way with $$Y = \sum_{i=1}^{N} x_i s_i c_i^t + B, \quad (4)$$

where Y and B are matrices. Since this system is linear, it can be rewritten according to the equation y=Hx+b (5), where y and b are columns-vectors, $x=[x_1 \ldots x_N]^t$ represents the variables to be calculated that are the protein concentrations, and H is a matrix formed by juxtaposing columns-vectors $y_i$ that correspond to signals that would give the respective protein i to a unit concentration. H is parameterized by all the factors involved in the measurement, at least some of them of which being able to be considered as uncertain and being likely to be calculated again.

A Bayesian analysis of factors considered as uncertain is carried out by estimating these factors as probability distributions, called a posteriori probability distributions, one parameter of which gives the final estimation of the factors and of the protein concentrations and finally the molecular profile of the sample.

From the a priori values, before this estimation, factors will be able to be obtained through the measurement or through hypotheses considered as likely, such as a priori probability distributions.

First Example

In the first example, which however does not form part of the invention, a nearly direct estimation of the concentrations is carried out by assuming that most of the factors included in the modelling function of the measurement signal are known without uncertainty, except for the noise that is modelled by an a priori Gaussian probability distribution whose average is assumed to be zero (which means that the measurement line does not make systematic errors) and whose variance is $\sigma_b^2$, chosen by a user according to its own experience or assessed by, for example, a spectral analysis measurement, on the equipment without load as necessary. A good assessment will of course give more reliable results but even an approximate assessment is likely to improve the assessment with respect to a direct measurement. Finally, the noise is considered as blank.

Let $\theta$ be the set of variables involved in the model, the a priori probability distribution of the signal y (as a function of x and $\theta$) of (5) can be described by (6)

$$p(y \mid x, \theta) = \frac{1}{\left(\sigma_b \sqrt{2\pi}\right)^M} \exp\left(-\frac{1}{2} \frac{\|y - Hx\|^2}{\sigma_b^2}\right),$$

that gives the probability value for any value of y as a function of H and x.

The a priori probability distributions for the protein concentrations can be represented by a Gaussian density function of the equation (7)

$$p(x) = \frac{1}{\left(\sigma_x \sqrt{2\pi}\right)^N} \exp\left(-\frac{1}{2} \frac{\|x - x_0\|^2}{\sigma_x^2}\right),$$

where $x_0$ is the most probable value measured from the peak height or another information source as a previous experiment, or on a series of such experiments related to different samples coming from different people, or from different sick people, etc.; and the variance $\sigma_x^2$ is chosen by the user to express the reliability he/she allocates to the first measurement. His/her studies can be based on values measured beforehand for different samples, and which have thus yielded known statistical distributions, on which the a priori probability distribution should adjust. The average equal to $x_0$ of the function expresses that the real values should be close to the measured values and that there is no correlation between the different protein concentrations.

The a posteriori probability distribution for the variable x can then be determined by the equation (8) from (6) and (7):

$$p(x \mid y, \theta) \propto \exp\left(-\frac{1}{2} \frac{\|y - Hx\|^2}{\sigma_b^2} - \frac{1}{2} \frac{\|x - x_0\|^2}{\sigma_x^2}\right),$$

where the symbol infinite means here a proportionality.

The last step of the method consists of giving an estimation of x according to this a posteriori probability distribution. Different criteria can be chosen; here, an estimation by the average $\hat{x}$ of the distribution is chosen, that is given by the equation (9)

$$\hat{x} = \left(H^t H + \frac{\sigma_b^2}{\sigma_x^2} I\right)^{-1} \left(H^t y + \frac{\sigma_b^2}{\sigma_x^2} x_0\right),$$

where I is the identity matrix, the parameters of the equation (9) being all known by either the measurement or the user determination. Other parameters, such as the median or the maximum, can also be recommended in some cases, depending upon the obtained probability distribution function a posteriori obtained.

Second Example

A more general example will now be described. As some fluctuation causes in the measurements cannot be perfectly controlled, nor all the modelling parameters be efficiently calibrated, it can be necessary to adjust some of them. In the following example, these parameters will be the standard deviation $\sigma_b$ of the a priori probability distribution of the noise b (already discussed in the previous example) and the width of the chromatographic peak, also noted here as the standard deviation $\sigma_c$. All the parameters of the vector $\theta$ will be called $\theta'$, and it will again be noted $\gamma_b = \sigma_b^{-2}$ and $\gamma_c = \sigma_c^{-2}$.

A priori probability distributions must be determined for these parameters $\gamma_b$ and $\gamma_c$. The Jeffreys function $p(\gamma_b)=\gamma_b^{-1}$ for the first one and a uniform distribution between two conventional values (chosen by the user) $\gamma_{c\ min}$ and $\gamma_{c\ max}$ for the second one can be chosen.

The a posteriori probability distribution for the variables [x $\gamma_b$ $\gamma_c$] as a function of $\gamma$ and $\theta'$ is given by the equation (10)
$p(x,\gamma_b,\gamma_c|\gamma,\theta') \propto p(x)p(\gamma_b)p(\gamma_c)p(\gamma|x,\gamma_b,\gamma_c,\theta')$ according to the Bayes rule. This distribution is no longer Gaussian, and its average will be estimated by a stochastic sampling method involving a random vector generator reproducing this distribution. Estimating the average will consist in obtaining, for each of the variables x, $\gamma_b$ and $\gamma_c$, the average of the values produced by this generator. A Gibbs structure that enables to transform the sampling of a multi-variable law into a sampling of single variable or Gaussian laws can be used. The algorithm of the generator will thus consist in initializing [x $\gamma_b$ $\gamma_c$] to values $x^{(0)}$, $\gamma_b^{(0)}$, $\gamma_c^{(0)}$ and for k ranging from 1 to K, consecutively generating $x^{(k+1)} \sim p(x|y,\gamma_b^{(k)},\gamma_c^{(k)})$, $\gamma_b^{(k+1)} \sim p(\gamma_b|y,x^{(k+1)},\gamma_c^{(k)})$, $\gamma_c^{(k+1)} \sim p(\gamma_c|y,x^{(k+1)},\gamma_b^{(k+1)})$, where the sign ~ means that the element on the left is randomly taken according to the probability distribution of the element on the right, for example by using the Metropolis-Hastings algorithm, or the random number generating algorithm.

These three probability distributions could respectively correspond to a multivariable Gaussian law $$p(x|y,\gamma_b,\gamma_c) = (2\pi)^{-\frac{N}{2}} |R|^{-\frac{1}{2}} \exp\left(-\frac{1}{2}(x-\mu^t)R^{-1}(x-\mu)\right)$$

with $\mu = (H_{\gamma_c}^t H_{\gamma_c})^{-1} H_{\gamma_c}^t y$, $R + \gamma_b^{-1}(H_{\gamma_c}^t H_{\gamma_c})^{-1}$, a gamma distribution $$p(\gamma_b|y,x,\gamma_c) = \frac{\gamma_b^{\alpha-1}}{\beta^\alpha \Gamma(\alpha)} \exp\left(-\frac{\gamma_b}{\beta}\right)$$

with
$\alpha = M/2, \beta = \|y - H_{\gamma_c} x\|^2 / 2$,
and $\Gamma$ is the gamma unction,
and a probability distribution $$p(\gamma_c|y,x,\gamma_b) \propto \exp\left(-\frac{1}{2}\gamma_b \|y - H_{\gamma_c}\|^2\right) \nu[\gamma_{c\ min};\gamma_{c\ max}](\gamma_c),$$

with $\nu$ that is the function indicative of the normalized interval [$\gamma_{c\ min}, \gamma_{c\ max}$], also called constant distribution on the interval.

This distribution can be sampled by a Metropolis-Hastings algorithm known to statisticians.

Third Example

Here below will be set out the third example which illustrates the situation where several factors of the measurement (gain of the system, retention time, besides noise) are considered as uncertain, being unstable from one measurement to another, and should be estimated by a probabilistic method. These factors are put together into a vector of unstable factors $\theta_{unstable}$ that is generated through iterating by a Gibbs sampler, with a posteriori and conditional probability distributions. The different factors can be generated as follows:

1) The vector $x^{(k)}$ expressing the height of the peaks and that is involved also in the method, can be obtained by a multinormal law generator of average $(H'H)^{-1}(H'y - H'H^* x^*)$ and of covariance matrix $\sigma_b^2 (H'H)^{-1}$.

2) The factor $\xi^{(k)}$ which is the result from the concatenation into column-vector of the content of the matter $\Xi_i$ of the equation (3) (system gain) is obtained with the multinormal law generator of average $(G'G)^{-1}(G'y)$ and of covariance matrix $\sigma_b^2 (G'G)^{-1}$ coming from another way to write the equation (3): $y = G\xi + b$.

3) The retention times $T_i$ in the chromatographic column are also part of unstable parameters, and each $T_i$ is generated by an independent Metropolis-Hastings algorithm:

Generate $T' \sim \nu[T_{i\ min}; T_{i\ max}]$ and $u \sim \nu_{[0:1]}$
Calculate $$\delta_1 = \left(-\frac{1}{2}\sigma_b^{-2}\{\Delta_{1i} - \Delta_{2i}\}\right)$$

with
$\Delta_{1i} = \Psi(x^{(k)}, \xi^{(k)}, [T_1^{(k)} \ldots T_{i-1}^{(k)} T', T_{i+1}^{(k-1)} \ldots T_1^{(k-1)}])$ $\Delta_{2i} = \Psi(x^{(k)}, \xi^{(k)}, [T_1^{(k)} \ldots T_{i-1}^{(k)} T_i^{(k-1)} T_{i+1}^{(k-1)} \ldots T_1^{(k-1)}])$ If $\delta > \log(u)$
then $T_i^{(k)} \leftarrow T'$
else $T_i^{(k)} \leftarrow T_i^{(k-1)}$ It is recalled that $\Psi$ is the vector of the variables $\Psi_i$, equal to $$\Psi(x, \xi, T) = \| Y - \sum_{p,i,j} (x_p D_{ip} \Xi_i \pi_{ij} s_{ij} c_i^t(T_i) + x_p^* D_{ip} \Xi_i \pi_{ij} s_{ij}^* c_i^t(T_i)) \|^2.$$

4°) Finally, $\sigma_b^{-2(k)}$ is obtained by a gamma law generator of the density $$p(\sigma_b^{-2}) = \frac{\sigma^{-2(\alpha-1)}}{\beta^\alpha \Gamma(\alpha)} \exp\left(-\frac{\sigma_b^{-2}}{\beta}\right)$$

with $$\alpha = NM/2; 1/\beta = \Psi(x,\xi,t)/2.$$

The resolution consists of obtaining values of this random generator and applying them the estimation criterion decided beforehand, such as the average. When this criterion converges, the results being searched for will be obtained.

The a posteriori probability distributor is:

$$p(x, \xi, t, \gamma_b'', \theta'' \mid y) = p(y \mid x, \xi, t, \gamma_b, \theta'') p(x) p(\gamma_b) p(\xi) \prod_i p(T_i)$$

with $p(y|x,\xi,t,\gamma_b,\theta'') = p(y|x,\theta)$
and $p(x)$ as in the first example,
$p(\gamma_b)$ identical to that of the second example, $$p(\xi) = \frac{1}{(\sigma_\xi \sqrt{2\Pi})^N} \exp\left(-\frac{1}{2} \frac{\|\xi - \xi_0\|^2}{\sigma_\xi^2}\right);$$

$\xi$ is the value known from previous experiments, or the gain value calculated from the estimated height of the peak and the known value of x on this experiment or similar experiments, or an arbitrary value, for example 0, if the value of the standard deviation tends to infinity or to a very high value with respect to the standard deviation of the noise; $\sigma_\xi$ is an interval for searching for $\xi_i$. It must encompass all the known values of $\xi_i$; $p(T_i)$ is the uniform distribution chosen between two values $T_{i\,min}$ and $T_{i\,max}$ chosen so as to encompass all the known values of $T_i$. In the extreme, they can be chosen so as to encompass the whole signal.

Fourth Example

Here is yet a fourth example. Here, we are looking to obtain certain factors of the analytical model that are supposed to be stable, that is constant from one measurement to another. It can be proportions $\Pi_i$ of molecules of each chemical species according to the number of charges; these proportions are assumed to depend on the solvent used in the measurement to move the sample in the chromatographic column.

Then, a distant calibration measurement of the principal measurement is carried out, by injecting a known amount of the chemical species considered into the equipment, reproducing the other conditions of the principal measurement, so that x is known. The algorithm of the fourth example enables $\Pi_i$ to be obtained.

Some factors as the gain of the digestion system $D_{ip}$, and the standard deviations expressing the width of the peaks in the chromatograph 3 and the mass spectrometer 4, $\sigma_{ci}$ and $\sigma_{si}$, are assumed to be known. Otherwise, the method could still be applied. It can be implemented the following way.

1) The vector $\xi^{(k)}$ is obtained with a multinormal law generator identical to that of the previous example.

2°) $t^{(k)}$ can still be obtained by an independent Metropolis-Hastings algorithm similar to that of the previous example.

3°) Each element of $\Pi_i^{(k)}$ can be generated by an independent Metropolis-Hastings algorithm.

4°) $\sigma_b^{-2(k)}$ is obtained by a gamma law generator of density $$p(\sigma_b^{-2}) = \frac{\sigma_b^{-2(\alpha-1)}}{\beta^\alpha \Gamma(\alpha)} \exp\left(-\frac{\sigma_b^{-2}}{\beta}\right),$$

where
$\alpha = NM/2; 1/\beta = \phi(t,\xi,\pi)/2$, according to an algorithm known to statisticians.

Here is the algorithm for carrying out part 3°.
Generate $\Pi' \sim D(\overline{\pi}_i; \sigma_{\pi_i}^2)$ and $u \sim \nu_{[0;\,1]}$, D Dirichlet distribution of average $\overline{\Pi}$, of variance $\sigma_{\pi_i}^2$.
According to the algorithm,
calculate $$\delta_i = \left(-\frac{1}{2}\sigma_b^{-2}\{\Delta_{1i} - \Delta_{2i}\}\right)$$

with $\Delta_{1i} = (t^k, \xi^{(k)}, [\Pi_1^{(k)} \ldots \Pi_{i-1}^{(k)} \Pi'_i \Pi_{i+1}^{(k-1)} \ldots \Pi_1^{(k-1)}])$ $\Delta_{2i} = (t^k, \xi^{(k)}, [\Pi_1^{(k)} \ldots \Pi_{i-1}^{(k)} \Pi_i^{(k-1)} \Pi_{i+1}^{(k-1)} \ldots \Pi_1^{(k-1)}]);$ if $\delta_i > \log(u)$,
then $\Pi_i^{(k)} \leftarrow \Pi'_i$;
else $\Pi_i^{(k)} \leftarrow \Pi_i^{(k-1)}$
with $$(x, T, \xi, \Pi) = \left\| Y - \sum_{p,i,j}(x_p D_{ip} \Xi_i \Pi_{ij} s_{ij} c_j^t(T_i) + x_p^* D_{ip} \Xi_i \Pi_{ij} s_{ij}^* c_i^t(T_i)) \right\|^2$$

where x is the concatenation of the values $x_i$, and the matrix $\Pi$ is the concatenation of the vectors $\Pi_i$ estimated by the algorithm and formed themselves by the elements $\pi_{ij}$.

The probability distributions of these factors x, $\xi$, t, $\Pi_i$ and b are converged by consecutive iteration loops, as in the third example. When the probability distribution of $\Pi_i$ has converged, it can be used in the principal measurement and the conditions of the previous examples, for example in the function $\Psi_i$ in the third example.

Such a calibration could be applied for determining other factors considered to be stable, such as $\sigma_{si}$ and $\sigma_{ci}$ under certain conditions.

The method can be completed by some refining. The isotopic marking can also be used by associating synthetic molecules of known concentration, carrying a certain number of isotopes, with each molecule of interest. As the molecule of interest and the calibration molecule have substantially the same physical or chemical properties, some parameters can be found again. It can be the gain $\Xi_i$ of the measurement apparatus or other parameters such as the retention time $T_i$ of the molecules of interest. An external calibration can be carried out by measuring the molecules of known concentration in a simplified environment to know some parameters of the model.

The a priori probability distributions with which the calculation of certain factors is started up can include the known statistical functions represented by their parameters, such as a centre value and a standard deviation, or a variation interval between two end values. The invention can be extended to multi-dimensional chromatographies. The data of the matrix H will then be a tensor rather than a matrix. Finally, the invention can be extended to molecules other than proteins.

Figure 3:
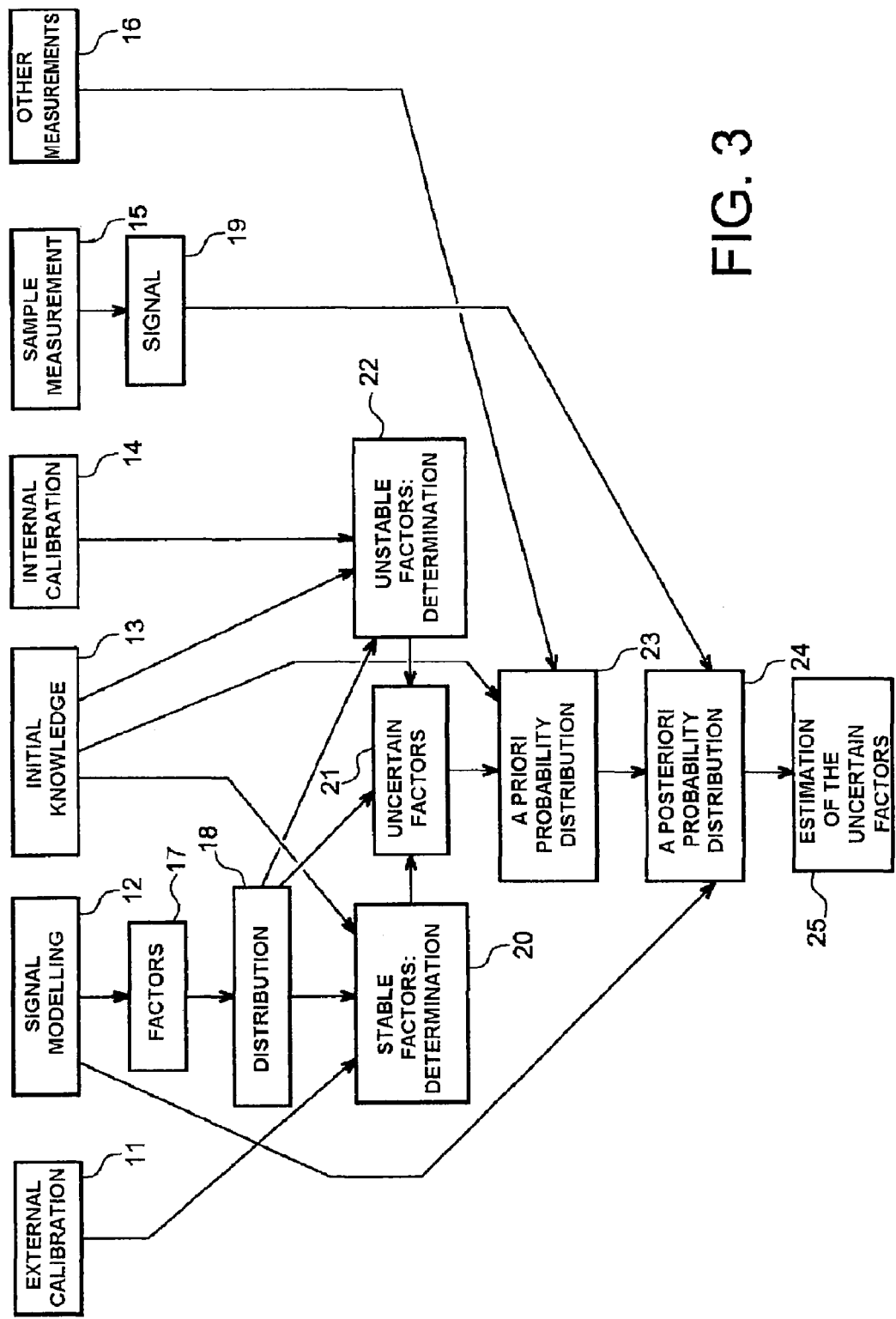

FIG. 3 summarizes the method. The tools used, corresponding to a first level of the method, include the external calibration 11, the signal modelling 12, the initial knowledge 13, the internal calibration 4, the sample measurement 15 and possibly other measurements 16. From the signal modelling 12, the factors 17 included in this modelling is inferred, and from the sample measurement 15, the signal 19 is inferred. The factors 17 are subjected to a distribution 18 into stable factors 20, and certain factors 21 and unstable factors 22. The stable factors 20 can be determined with an external calibration 11 and initial knowledge 13. The unstable factors 22 can be also determined by the initial knowledge 13 and the external calibration 14. Some other factors, both stable and unstable, are however uncertain factors, that are modelled with an a priori probability distribution 23 still set up by the initial knowledge 13 and possibly by the other measurements 16. Applying detailed calculation steps into the body of this document yields a posteriori probability distributions of the uncertain factors thanks to the signal modelling 12 and the signal 19. Estimating the uncertain factors 25 has become possible.

The invention claimed is:

1. A method for estimating molecule concentrations in a sample, said method comprising:
    obtaining a signal generated by a sample analyzing apparatus, said signal including at least one spectrum, the spectrum including peaks representative of the molecule concentrations in the sample and being expressed as a function of at least one variable;
    obtaining an analytical modeling of the signal with a modeling function, wherein the modeling function is based on the molecule concentrations and factors including gain factors of the sample analyzing apparatus and description factors of the peaks;
    selecting uncertain factors in said factors;
    determining a priori probability distributions for the uncertain factors and the molecule concentrations;
    establishing, with the modeling function and the signal, posteriori probability distributions for the molecule concentrations and the uncertain factors; and
    estimating, with a processing module, the molecule concentrations and the uncertain factors from a parameter inferred from the posteriori probability distributions.

2. The method of claim 1, wherein the description factors of the peaks include shape description factors of the peaks.

3. The method of claim 2, wherein the shape description factors include widths of the peaks.

4. The method of claim 1, wherein the uncertain factors include retention times of the molecules in a chromatographic column.

5. The method of claim 1, wherein the uncertain factors include the gain factors.

6. The method of claim 1, wherein the parameter inferred from the posteriori probability distributions is an average value.

7. The method of claim 1, wherein the parameter inferred from the posteriori probability distributions is a median value.

8. The method of claim 1, wherein the parameter inferred from the priori probability distributions is a maximum value.

9. The method of claim 1, wherein at least one of the priori probability distributions includes a Gaussian function.

10. The method of claim 1, further comprising:
    implementing an internal calibration, which includes injecting marker molecules into the sample, the marker molecules having properties similar to certain of the molecules of the sample inasmuch they provide measurement peaks similar to measurement peaks of said molecules of the sample.

11. The method of claim 1, further comprising:
    implementing an external calibration, which includes injecting molecules similar to certain of the molecules of the sample, with known concentrations, into the sample analyzing apparatus, and inferring certain of the factors from the signal obtained from said injecting and from the analytical modeling.

12. The method of claim 1, wherein the molecules are proteins.

13. A device comprising:
    a sample analyzing apparatus configured to analyze a sample and provides at least one signal that includes at least one spectrum, the spectrum including peaks representative of molecule concentrations which are expressed as a function of a variable; and
    a processing module configured to estimate the molecule concentrations in the sample, to obtain an analytical modeling of the signal with a modeling function, wherein the modeling function is based on the molecule concentrations and factors including gain factors of the sample analyzing apparatus and description factors of the peaks, to identify uncertain factors in said factors, to determine priori probability distributions for the uncertain factors and the molecule concentrations, to establish, with the modeling function and the signal, posteriori probability distributions for the molecule concentrations and the uncertain factors, and to estimate the molecule concentrations and the uncertain factors from a parameter inferred from the posteriori probability distributions.

14. The device of claim 13, wherein the sample analyzing apparatus includes a chromatographic column.

15. The device of claim 13, wherein the sample analyzing apparatus includes a mass spectrometer.

16. The device of claim 13, wherein the sample analyzing apparatus includes an upstream device for breaking down proteins.

* * * * *